United States Patent [19]

Deutsch et al.

[11] Patent Number: 4,795,626

[45] Date of Patent: Jan. 3, 1989

[54] $^{99m}$TC$^{(III)}$ MYOCARDIAL IMAGING AGENTS WHICH ARE NON-REDUCABLE IN VIVO

[75] Inventors: Edward A. Deutsch, Cincinnati, Ohio; Jean-Luc Vanderheyden, Seattle, Wash.

[73] Assignee: University of Cincinnati, Cincinnati, Ohio

[21] Appl. No.: 172,969

[22] Filed: Mar. 11, 1988

Related U.S. Application Data

[63] Continuation of Ser. No. 733,680, May 10, 1985, abandoned.

[51] Int. Cl.$^4$ .................... A61K 49/02; C07F 13/00
[52] U.S. Cl. .................................... 424/1.1; 424/9; 534/14
[58] Field of Search .................. 424/1.1, 9; 534/14

[56] References Cited

U.S. PATENT DOCUMENTS

| | | | |
|---|---|---|---|
| 4,374,821 | 2/1983 | Glavan et al. | 424/1.1 |
| 4,452,774 | 6/1984 | Jones et al. | 534/10 X |
| 4,455,291 | 6/1984 | Tweedle | 534/14 X |
| 4,489,054 | 12/1984 | Deutsch et al. | 424/1.1 |
| 4,497,790 | 2/1985 | Rodriguez | 424/1.1 |
| 4,512,967 | 4/1985 | Linder | 424/1.1 |
| 4,582,700 | 4/1986 | Dean et al. | 534/14 X |
| 4,746,505 | 5/1988 | Jones et al. | 534/14 X |

FOREIGN PATENT DOCUMENTS

| | | |
|---|---|---|
| 0063946 | 11/1982 | European Pat. Off. |
| 0123240 | 10/1984 | European Pat. Off. |

OTHER PUBLICATIONS

G. Bandoli et al, "Synthesis and Characterization of Technetium (V) Complexes with Tridentate Schiff Base Ligands. X-Ray Crystal Structure of Chloro [N-2-hydroxyphenyl) salicylideneiminatol] oxotechnetium(V)", Inorganica Chimica Acta, 95 (1984) 217-223.

M. B. Cingi et al, "Technetium-Phosphine Complexes. Diethylphenylphosphonite Complexes of Technetium (III) and Mixed Ligand Complexes of Technetium(I) With Carbonyls and Diethylphenylphosphonite, and Crystal and Molecular Structure of cis-Dicarbonyltetrakis (diethylphenylphosphonite) Technetium(I) Perchlorate", Inorganica Chimica Acta, 13 (1975) 47-59.

S. Jurisson et al, "New Oxotechnetium(V) Complexes of N,N'-Ethylenebis(acetylacetone imine), N,N'-Ethylenebis)salicylideneamine) and o-Phenylenebis(-salicylidenamine). X-ray Structures of the Complexes of N,N'-Ethylenebis(acetylacetone imine) and N,N'-Ethylenebis(salicylideneamine)", Inorganic Chemistry, vol. 23, No. 2, 1984, 227-231.

M. J. Abrams et al, "The Synthesis and Characterization of Hydrotris (1-pyrazolyl)borate Complexes of Technetium(III) and Rhenium(V) and (III)", Inorganica Chimica Acta, 82 (1984) 125-128.

*Primary Examiner*—John F. Terapane
*Assistant Examiner*—Virginia B. Caress
*Attorney, Agent, or Firm*—Wood, Herron & Evans

[57] ABSTRACT

A cationic $^{99m}$Tc$^{III}$ myocardial imaging agent is disclosed which has a relatively negative redox potential. This prevents in vivo reduction of the Tc(III) to Tc(II). The redox potential of the Tc(III) is controlled by complexing the Tc with both hard and soft atoms. Preferably four of the atoms complexed to the Tc(III) are hard atoms such as nitrogen or oxygen and the remaining two are soft atoms such as phosphorous or arsenic. These imaging agents are particularly useful in imaging the human heart.

25 Claims, No Drawings

$^{99m}TC^{(III)}$ MYOCARDIAL IMAGING AGENTS WHICH ARE NON-REDUCABLE IN VIVO

Part of the work leading to the present invention was funded by the U.S. Department of Health and Human Resources; the U.S. Government is granted a royalty free nonexclusive license.

This application is a continuation of application Ser. No. 733,680, filed May 10, 1985 now abandoned.

BACKGROUND OF THE INVENTION

Several noninvasive methods of imaging body organs have been developed over the past decade. These procedures are based on the tendency of a body organ to concentrate some detectable chemical. Particularly useful chemicals are those which emit gamma radiation. Subsequent scanning of the organ with a gamma ray camera provides an image of the organ from which diagnostic information can be obtained. $^{99m}Tc$(Tc-99m) has found particular utility in this area because of its half-life and gamma ray emission.

The metastable isotope Tc-99m has a six hour half-life and an emission spectrum of 99% gamma radiation at 140 KeV and has a specific activity $5.28 \times 10^9$ millicuries per gram. Tc-99m has also become readily available in hospitals through the use of selective elution from a molybdenum-99 generator. The isotope Mo-99 produces Tc-99m as a radioactive decay product.

Although detecting radiation from a radiation emitting pharmaceutical has proven particularly useful in noninvasive organ imaging, particular radiopharmaceuticals are still needed. There is a particularly strong need for an effective myocardial imaging agent. There are two types of myocardial imaging agents, the positive agents which accumulate in an infarcted area and negative agents which accumulate in a normal heart but not in the infarcted area. Using a positive agent causes an infarcted area to show up as a hot spot of radioactivity whereas with a negative agent the infarcted area shows up as a cold area against a hot background.

Over the past couple of years several different Tc-99m compounds have been disclosed for use as positive myocardial imaging agents. These different imaging agents, having substantially different chemistry, have found various levels of utility in different mammals. To date it is still a goal of nuclear medicine to find a more effective negative myocardial imaging agent particularly suited for the human heart.

The first work with myocardial imaging agents formed from Tc-99m was conducted by Deutsch et al as disclosed in U.S. Pat. No. 4,489,054. Deutsch et al determined that cationic lipophilic complexes of Tc-99m provided a useful myocardial image in mammals. This work provided particularly good images with certain mammals particularly dogs. Technetium can assume several valence states ranging from +7 to −1. The methods disclosed in the Deutsch et al U.S. Pat. No. 4,489,054 disclosed technetium complexes in the +3 state. These subsequently were found to provide a relatively poor image of the human heart.

Further work conducted by Deutsch, Libson et al indicated that the complexes of Tc(I)-99m provided more useful heart images. These provided particularly good images of cat hearts. Unfortunately with humans these images were obscured by the accumulation of the technetium complex in the liver. This interfered with obtaining a very good image of the heart. This is disclosed in Deutsch et al U.S. application Ser. No. 628,482 filed July 6, 1984 incorporated herein by reference. Additional work disclosed in Deutsch et al application Ser. No. 628,482 filed July 6, 1984 indicated that $^{99m}Tc$(I) compounds when ligated to phosphonate and phosphonite ligands cleared the liver more quickly and provided an even better myocardial image. These clear the liver exceptionally well but do not clear from the blood to permit a useful image of the heart. Other cationic ligated complexes of $^{99m}Tc$ are disclosed for example in Rodriguez U.S. Pat. No. 4,497,790; Glavan et al U.S. Pat. No. 4,374,821; and Tweedle U.S. Pat. No. 4,455,291. Other technetium compounds are disclosed in European patent application 0123240.

SUMMARY OF THE INVENTION

The present invention is premised upon the realization that in fact certain $^{99m}Tc$(III) compounds act as negative myocardial imaging agents for humans better than any of the known technetium compounds. The invention more basically is premised on the realization that known $^{99m}Tc$(III) compounds although providing heart images tend to be reduced somewhere in the human body subsequent to injection. This interferes with providing a useful myocardial image in a human. However $^{99m}Tc$(III) compounds with a reduction potential substantially more negative than known $^{99m}Tc$(III) compounds are not reduced in vivo and provide an excellent human heart image. More specifically the present invention is premised upon the realization that cationic $^{99m}Tc$(III) compounds having a redox potential $E^{0\prime}$, Tc(III/II), about at least as negative as −0.3 volts using an aqueous Ag/AgCl electrode and a platinum wire as reference and auxiliary electrodes respectively in N,N'-dimethylformamide(DMF) with 0.5M tetraethylammoniumperchlorate(TEAP) as a supporting electrolyte are not reduced in vivo. The redox potentials for the Tc(III/II) couple of complexes made according to the present invention are substantially more negative than prior art Tc(III) complexes used in myocardial imaging.

In order to provide a $^{99m}Tc$(III) compound having a sufficiently negative reduction potential for use in the present invention preferably 3 or 4 of the six atoms coordinatively bonded to the hexadentate Tc(III) center will be hard atoms such as oxygen, nitrogen, chlorine, or tetravalent carbon with the remaining two or three sites bonded to soft atoms such as the phosphorus in the trimethylphosphine ligand.

The invention is further premised on the realization that unique complexes of hexadentate $^{99m}Tc$(III) can be formed wherein the four atoms coordinatively bonded to the technetium in the planar positions are hard atoms and wherein the two atoms coordinatively bonded to the technetium in the axial position are soft atoms. This provides a unique method of forming a compound having a desired reduction potential. This method is uniquely suitable for forming a complex from either two bidentate ligands or one tetradentate or tridentate ligand wherein the remaining coordination bonding sites of the technetium are filled with soft ligands which are part of monodentate ligands such as alkyl phosphines and the like.

Because these complexes are not reduced in vivo to Tc(II) they provide excellent heart imaging agents and particularly useful heart imaging agents for humans.

DETAILED DESCRIPTION OF THE INVENTION

The technetium compounds which are useful as myocardial imaging agents in humans are hexadentate technetium complexes which have an overall cationic charge. More specifically, the complexes will be technetium complexes in the +3 oxidation state coordinatively bonded to six atoms as shown in Formula 1.

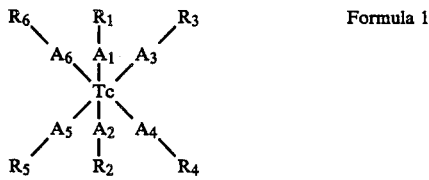

Formula 1

The atoms $A_1$ and $A_2$ are bound to technetium in the axial positions whereas $A_3$, $A_4$, $A_5$ and $A_6$ are bonded to technetium in the planar positions. In this complex at least three of $A_1$, $A_2$, $A_3$, $A_4$, $A_5$ and $A_6$ are hard atoms. Hard atoms are atoms which are more electronegative than the Tc(III) center and accordingly donate electrons to the Tc center. Specific hard atoms include oxygen, nitrogen, chlorine, and tetravalent carbon. Moderately hard atoms include sulfur and bromine. Preferably four of these atoms $A_1$-$A_6$ are hard or moderately hard atoms. The remaining two or three atoms must be soft atoms. Soft atoms are atoms which will accept electron density from technetium. These atoms would include phosphorous, arsenic, antimony, tellurium, selenium and bivalent carbon atoms such as in CO and isonitrile. The soft atoms provide a technetium complex which has a less negative reduction potential than a complex bonded to the hard atoms.

$R_1$-$R_6$ represent moieties bonded to the complexing atoms $A_1$-$A_6$. The A—R combined may represent a single ligand. The moieties represented by $R_1$-$R_6$ may represent multiple substituents as with the ligand trimethylphospine where A represents phosphorous and R represents three methyl groups. Further two R moieties can be bonded to each other, and where the ligand is $Cl^-$, A—R would represent only one atom.

For use in the present invention the redox potential for the Tc(III/II) couple of the cationic technetium complex myocardial imaging agent must be sufficiently negative to prevent the reduction to Tc(III) in vivo and must be more negative than about −0.3 volts versus a Ag/AgCl reference electrode in N,N' dimethylformamide and 0.5 M tetraethylammoniumperchlorate(TEAP) as supporting electrolyte. More preferably the complex will have a redox potential at least as negative as −0.4 V and more preferably −0.8 V. Increasing the number of hard atoms complexed to the Tc makes the reduction potential more negative. Of course the hardness of the complexing atoms contributes to the increase in negativity of the reduction potential. If more than four hard atoms are present, the complex tends to remain at Tc(IV) or Tc(V) and does not provide a useful image. This is particularly true with very hard atoms such as nitrogen, oxygen and chlorine.

The sign convention used for the reduction potentials is that adopted at the time of the XVII Conference of the International Union of Pure and Applied Chemists. Potentials increase towards systems of higher oxidizing power.

Further the cationic Tc complexes useful as myocardial imaging agents must be lipophilic but cannot be excessively lipophilic or else the will bind to proteins in the blood and provide only a blood pool image. The term lipophilic as used in this invention implies that the ligands and complexes derived therefrom have a balance of lipophilic and hydrophilic characteristics. These complexes are neither totally soluble in nonpolar water immiscible organic solvents nor are they totally soluble in polar organic water miscible solvents or water. The gradation of lipophilicity of the complexes of the present invention can be established by reference to partition coefficients using n-octanol/water, n-octanol/buffer or n-octanol/saline(Kung and Blau, J. Nucl. Med., 21, 147–152(1980)). In general, those cationic lipophilic complexes of Tc-99m having an n-octanol/saline partition coefficient greater than about 0.05 and less than about 20–25 are useful in the present invention.

Tc-99m complexes formed with three or four hard complexing atoms can be formed from a variety of different ligand systems. These complexes can be formed from either tetradentate or tridentate ligands wherein at least three of the complexing atoms of the complex are hard atoms. These can also be formed from bidentate ligands wherein both of the bidentate ligands donate hard atoms. Another method is the use of a tetradentate ligand where only one or two of the complexing atoms are hard atoms with the remaining two or three complexing atoms being soft atoms. In this last possibility the additional one to three hard atoms required to provide the requisite reduction potential can be provided by a second ligand system, particularly monodentate ligands such as a chloride ion.

Where the complex of the present invention is formed from a tridentate or a tetradentate ligand having at least three hard atoms, a two step method is used to prepare the complex.

In the first step $^{99m}TcO_4^-$ (pertechnetate) having an oxidation state of +7 is reduced to technetium +5 having a formula $^{99m}Tc^VO(L)^+$. This is formed by heating $^{99m}TcO_4^-$ in the presence of the tridentate or tetradentate ligand and a reducing agent such as stannous chloride or sodium borohydride. In the second step the $^{99m}Tc(V)$ complex is further reduced by treating it with a ligand having soft atoms such as trimethylphosphine. This is carried out by heating the $^{99m}Tc(V)$ complex in the presence of the ligand. A chemical reducing agent such as borohydride salts, stannous ion salts or hyposulfite salts can also be added.

More particularly the pertechnetate solution is obtained from a 99-Mo generator. This method of obtaining $^{99m}Tc$ is well known to those skilled in the art and is disclosed for example in Deutsch et al U.S. Pat. No. 4,489,054 incorporated herein by reference. This is also disclosed in Glavan et al U.S. Pat. No. 4,374,821 also incorporated herein by reference.

The $^{99m}Tc$ complex is formed from the $^{99m}TcO_4^-$ solution obtained from the molybdenum generator. This pertechnetate can be diluted to the desired radioactive concentration of 10–100 mCi/mL with normal saline. A solution of ligand and a reducing agent are added to the $^{99m}TcO_4^-$ to cause reduction of the pertechnetate and formation of the Tc(V) complex. This reduction is conducted under anaerobic conditions. The Tc(V) complex is extracted from the saline solution with, for example, methylene chloride. Alternately, a cation exchange resin may be used for purification.

Where the ligand is a tetradentate ligand the formed Tc(V) complex will have the following general formula:

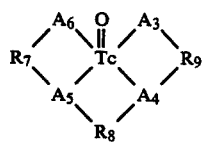 Formula 2 wherein at least 3 and preferably all of $A_3$, $A_4$, $A_5$ and $A_6$ represent hard (or moderately hard) atoms specifically tetravalent carbon, oxygen, nitrogen, sulphur(in a planar position), chlorine or bromine and one of $A_3$–$A_6$ may represent a soft atom such as phosphorous or arsenic or divalent carbon. $R_7$, $R_8$ and $R_9$ represent $C_1$–$C_4$ alkylene, $C_1$–$C_4$ alkenyl or arylene groups which may be substituted with hydroxyl, aldehyde, ketone, ester, amide, carbohydrate or ether groups, or $C_1$–$C_4$ alkylene-arylene groups or groups substituted with hydroxyl, aldehyde, ketone, ester, amide, carbohydrate or ether groups. Comparing this to formula 1, it is apparent that $A_3$–$R_3$, $A_4$–$R_4$, $A_5$–$R_5$ and $A_6$–$R_6$ combine to represent the tetradentate ligand:

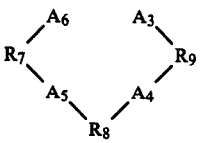 Formula 3

Particularly suited tetradentate ligands are shown in table 1. One preferred type of ligand are Schiff base ligands.

TABLE 1

| Generic | Preferred |
|---|---|
| | N,N′—ethylenebis(acetylacetone iminato) = (acac)$_2$en |
| | N,N′—ethylenebis(tert-butyl acetoacetate iminato) = (buac)$_2$en |
| | N,N′—ethylenebis(benzoylacetone iminato) = (bzac)$_2$en |
| | N,N′—ethylenebis(3-bromoacetyacetone iminato) = (brac)$_2$en |
| | N,N′,methyl-ethylenebis(acetylacetone iminato) acac$_2$pn |
| | N,N′—ethylenebis(salicylidene aminato) = (Sal)$_2$en |

Prepared according to Inorganic Chemistry 23, 4743(1984) and Inorganic Chemistry 23, 227(1984)

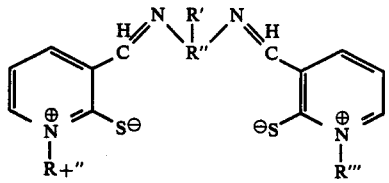

Prepared according to method discussed in Inorganic Chemistry 23, 271(1984)

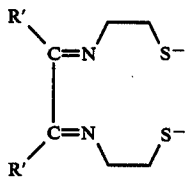   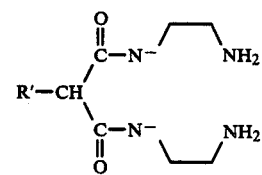

R′ represents H, hydroxyl, $C_1$–$C_5$ alkyl, $C_1$–$C_5$ alkyl substituted by hydroxyl, ether, amide ester, ketone, aldehyde or nitrile group.

R″ represents $C_1$–$C_4$ alkylene, $C_1$–$C_4$ alkenyl which may be substituted with hydroxyl, ether, amide, ester, ketone, aldehyde or nitrile group.

R‴ $C_1$–$C_5$ alkyl, $C_1$–$C_5$ alkyl substituted by hydroxyl ether, amide, ester, ketone, aldehyde or nitrile groups When the ligand used to formulate the Tc(V) complex is a tridentate ligand the formed Tc(V) complex will have the following general formula:

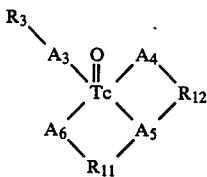

Formula 4 wherein $A_4$, $A_5$ and $A_6$ represent hard atoms and $R_{11}$ and $R_{12}$ represent the same as $R_7$, $R_8$ and $R_9$. The ligand —$A_3$—$R_3$, generally represents —$OH^-$, —$OH_2$ or $Cl^-$ which in the preparation, is provided by the reaction medium. In this formula $A_4$—$R_4$, $A_5$—$R_5$ and $A_6$—$R_6$ combine to represent the ligand

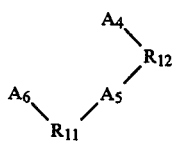

Formula 5

Exemplary tridentate ligand are shown in table 2. Preferably these ligands will also be Schiff base ligands.

TABLE 2

| Tridentate ligand | Preferred |
|---|---|
| 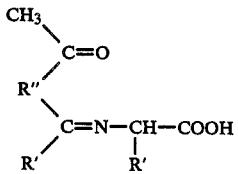 | R″ represents —$CH_2$—$CH_2$— or —$CH_2$—$CH_2$—$CH_2$— R′ represents H |
| H—X—R″—N—R″—XH <br> \| <br> R′ | R′ represents H or —$CH_3$ |
| 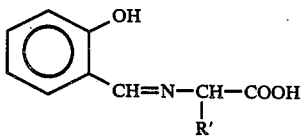 <br> Also enol form of the above formula | R″ represents —$CH_2$—, —$CH_2$—$CH_2$— or —$CH_2$—$CH_2$—$CH_2$— |

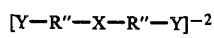

Discussed in Azuma U.S. Pat. No. 4,489,053

$[Y-R''-X-R''-Y]^{-2}$

Y represents —$NH_2$, —$OH$, —$\overset{O}{\underset{\|}{C}}$—$NH_2$ —$SH$, —$COOH$ or any of these groups with one hydrogen removed to form a negative charge
X represents O or S TABLE 2-continued R′ & R″ represent same groups listed in Table 1

The preparation of the Tc(V) complex is further described in example 1 wherein the ligand is $(acac)_2en^+$.

EXAMPLE 1

Preparation of $^{99m}Tc^VO(acac)_2en$

All steps are conducted under anaerobic conditions. A solution of $^{99m}TcO_4^-$ (obtained from a molybdenum generator) was diluted to 1.8 mL with normal saline in a 5 mL borosilicate vial (WHEATON) and 0.300 mL of 0.2 M ligand solution was added. 0.02 mL of a 0.02 M $SnCl_2$ solution in dry absolute ethanol, and then 0.02 mL of 1 M NaOH were added. The mixture was sealed with a Teflon lined cap and heated at 95°±2° C. for 15 minutes in a TECAM dry heat bath equilibrated to that temperature. The preparation was then cooled to ambient temperature using a stream of cold water. A 0.10 mL aliquot of 0.5 M $LiF_3CSO_3$ (pH=10.5) was added, followed by 3.0 mL of HPLC grade $CH_2Cl_2$, and another 0.02 mL aliquot of the $SnCl_2$ solution. The vial was then capped, vortexed for 1 minute, and finally centrifuged. The $CH_2Cl_2$ layer of the preparation was removed with a glass syringe and placed in a purged vial which was sealed with a Teflon lined cap. HPLC quality control of the preparation shows a greater than 95% radiochemical yield; the $CH_2Cl_2$ extraction yield is 50-70%.

According to the present invention a myocardial imaging agent is prepared by reducing the Tc(V) complex to a Tc(III) complex. To accomplish this the $^{99m}Tc(V)$ complex (hereinafter referred to as the Tc stock solution) is combined with a soft atom containing ligand such as trimethylphosphine. The ligand is introduced as a gas or liquid or salt adduct with a Lewis acid. At ambient or elevated temperature this acts to reduce the Tc(V) complex to a Tc(III) complex. The Tc(III) complex can then be loaded onto a cationic exchange resin and eluted from the column with an 5% ethanol/water solution. The Tc(III) complex will have the following general formula:

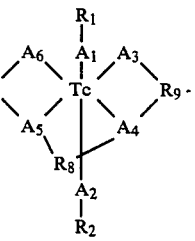

Formula 6 or

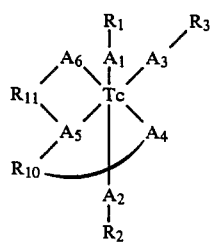

Formula 7

The production of $^{99m}Tcacac_2en(PMe_3)^+_2$ is further described in Example 2.

EXAMPLE 2

Preparation of $^{99m}Tc^{III}(acac)_2en(PMe_3)_2+$.

To a 5 mL borosilicate vial (WHEATON) was added ca. 50 mg of trimethylphosphine silver iodide salt (ALDRICH) in a glove bag. This vial was capped wihh a screw-cap Mininert valve. A 30 cm Teflon tube connected a platinum needle (HAMILTON) inserted in the Mininert valve to a second platinum needle that was inserted into the stock solution of $^{99m}TcO(acac)_2en+$ through the serum cap. The vial containing $PMe_3.AgI$ salt was then placed in a sand bath at 200°-250° C.; within 15 minutes the salt decomposed and produced $PMe_3$ as a gas. This gas was driven into the vial containing the stock solution; this second vial was kept in a 4° C. waterbath. After addition of $PMe_3$, the reaction mixture was kept at ambient temperature for 10 minutes, then rotoevaporated to dryness, and the residue was dissolved in 2 mL of water. This solution was then loaded onto a Sephadex SP C-25 cation exchange column (20×9 mm). The column was washed with 2 mL of water and 2 mL of a 5% ethanol/watrr solution and the desired product was then eluted in 85% yield with 2 mL of a 5% ethanol/saline solution. The final radiopharmaceutical solution was then filtered through an Acrodisk membrane filter.

EXAMPLE 3

Synthesis and purification of
$^{99m}Tc^{III}(acac)_2en[P(OMe)_3]_2+$

The $CH_2Cl_2$ stock solution of $^{99m}TcOacac_2en+$ was evaporated to dryness at ambient temperature under vacuum using a two way stopcock connector and the evacuated vial was filled with nitrogen. 0.5 mL of dry and degassed methanol and 0.1 mL of 10% $P(OMe)_3$ in methanol were added. The vial was heated at 50° C. for 45 minutes. Quality control via HPLC confirms ca. 95% yield. The purification of the reaction product was as follows: The product was diluted with 3 mL of degassed water. This solution was then loaded onto a $C_{18}$ Sep-pak cartridge previously prepared with 3 mL of 95% ethanol and 3 mL of water. The cartridge was then washed with 4 mL of 20% ethanol/saline mixture and the desired product eluted with 2 fractions of 2 mL 60% ethanol/saiine. The yield was ca. 50%. For in vivo testing, the preparation was filtered, diuuted to 15% ethanol/saline and injected into test animals as rapidly as possible.

EXAMPLE 4

Synthesis and purification of
$^{99m}Tc(acac)_2enY_2+$ (Y=(tert-butylisonitrile).

To the stock solution of $^{99m}TcO(acac)_2en+$ was added 0.25 mL of degassed 95% ethanol, 0.10 mL of 10% tert-butylisonitrile in dry ethanol and an aliquot of 0.20M $SnCl_2$ solution (0.10 mL). The mixture was heated in a vial at 50° C. for 40 minutes using a needle to allow evaporation of the methylenechloride in the stock solution. The preparation was then loaded onto a $C_{18}$ Sep-pak cartridge, and washed with 4 mL of 20% ethanol/saline. The radiopharmaceutical was eluted in 2 mL of 60% ethanol/saline with a yield of ca. 80%. The quality control shows the presence of an impurity(-5-10%) that has been identified as $^{99m}Tc(TBIN)_6+$. (TBIN=tert-butylisonitrile) The preparation was di- luted with water to 12% ethanol and loaded onto a Sephadex SP C-25 column (40×9 mm), washed with water and eluted with saline. The saline solution was filtered and used for animal studies. Radiochemical purity was ca. 90%.

A variety of monodentate ligands can be employed in the reduction of the Tc(V) complex to the Tc(III) complex. Ligands can be selected to alter the lipophilicity and redox potential of the formed complex. Particularly suitable ligands are isonitriles such as tert-butylisonitrile and arsenic and phosphorous compounds which have the following general formula:

where A is As or P and R represents $C_1$-$C_5$ alkyl, $C_1$-$C_5$ alkyl substituted by hydroxyl, ketone, aldehyde, nitrile, ether, amide or ether groups or oxy-$C_1$-$C_5$ alkyl such as the oxymethyl in trimethylphosphite. In the axial position sulfur compounds such as RSH act as soft atoms.

A Tc(III) complex can be made according to the present invention wherein bidentate ligands are used wherein the bidentate ligand includes two hard ligating atoms. Exemplary bidentate ligands are shown in Table 3.

TABLE 3

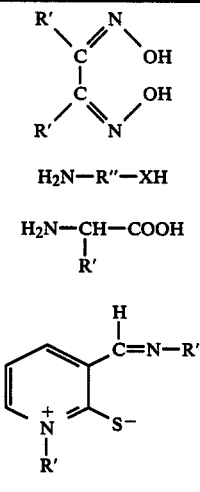

X represents same or different
—$NH_2$, —OH, —SH, —COOH, C(O)$NH_2$ (and anions derived from these groups) wherein total charge on ligand is −1
R' represents same group listed in Table 1

According to this method as intermediate $^{99m}Tc(V)O(L)_2+$ is formed wherein L represents the bidentate ligand. The method of forming the Tc(v) intermediate is the same as forming the Tc(V) intermediate with the tetradentate or tridentate ligands with the exception that twice the number of moles of ligand is added. this intermediate is then reduced to Tc(III) in the same manner as stated above. In this situation the Tc(V) intermediate will have one of the the following general formula:

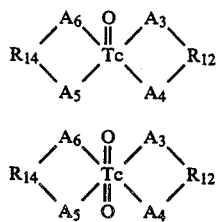

Formula 8 wherein $A_3$, $A_4$, $A_5$ and $A_6$ represent hard atoms and $R_{14}$ and $R_{13}$ represent the same moieties as $R_7$, $R_8$ and $R_9$. In this complex $A_3$—$R_3$ and $A_4$—$R_4$ combined represent $A_3$—$R_{13}$—$A_4$ and $A_5$—$R_5$ and $A_6$—$R_6$ combined represent $A_5$—$R_{14}$—$A_6$. $A_5$—$R_{14}$—$A_6$ will generally be the same as $A_3$—$R_{15}$—$A_4$. This Tc(V) complex formed by two bidentate ligands is reduced in the same manner that Tc(V) formed from tetradentate ligands to form a Tc(III) complex useful in the present invention and which has the following general formula:

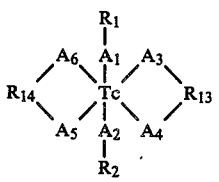

Formula 9

Alternately the technetium complex of the present invention can be formed from a mixed ligand system wherein the ligand system includes both hard and soft complexing atoms. The general formula for such ligands are shown in Formula 10(tetradentate) and 11(bidentate)

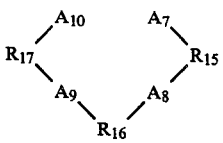

Formula 10 wherein some(most usually two) of $A_7$, $A_8$, $A_9$ and $A_{10}$ are soft atoms and the rest of said $A_7$, $A_8$, $A_9$ and $A_{10}$ are hard atoms. $R_{15}$, $R_{16}$ and $R_{17}$ represent the same moieties as $R_7$, $R_8$ and $R_9$ of formula 3. If the ligand system is a bidentate ligand system it will have the structure shown in formula 11:

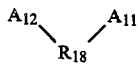

Formula 11 wherein $A_{11}$ is a hard atom, $A_{12}$ is a soft atom, and $R_{18}$ is the same as $R_{15}$, $R_{16}$, and $R_{17}$.

To make a complex useful in the present invention the ligands as shown in Formula 10 or 11 are simply brought into reaction with pertechnitate —99m according to the method disclosed in Deutsch et al U.S. Pat. No. 4387,087. As disclosed in that patent, a large stoichiometric excess of the ligand is combined with the $^{99m}TcO_4^-$. The reaction is carried out over a wide range of temperatures with the proviso that the aqueous phase should remain liquid throughout the preparation. Thus temperatures in the range of 0°–10° C. are used, most preferably 20°–80° C. The reaction time ranges from a few minutes to one to two hours. This treatment causes the pertechnetate to be reduced to form a composition having the following general formula: (when the tetradentate mixed ligand is used)

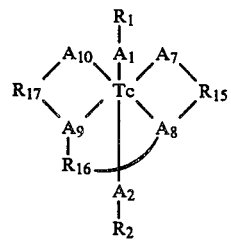

Formula 12 wherein $A_7$, $A_8$, $A_9$ and $A_{10}$ are complexing atoms donated by the mixed ligand and $A_1$—$R_1$ and $A_2$—$R_2$ represent ligands donated by the reaction medium. Generally $A_1$—$R_1$ and $A_2$—$R_2$ will represent chloride ion provided from the saline solution, or a hydroxide or water moiety provided by the solvent.

All the $^{99m}Tc(III)$ complexes described above are administered intravenously as radiopharmaceuticals in a radioactive dose of from 0.01 mCi/ml to 10 mCi/ml most preferably 2 mCi/ml–5 mCi/ml. The administration dose by weight of animal is 0.001 mCi/kg–1 mCi/kg preferably 0.002 mCi/kg–0.1 mCi/kg.

Imaging of the myocardium can be carried out by scanning techniques after waiting an appropriate period of time to permit blood clearance of the radiopharmaceutical. For example time dependent scintiscans of the chest region of a patient can be used. A computer interface 16 crystal, Ohio Nuclear Spectrometer can be used for these scans. The complexes of the present invention can also be used in a single photon emission computed tomography as described by Beyer et al, *Diagnostic Nuclear Medicine*, Volume 1, No. 2, page 10(summer of 1984). The use of certain of these complexes is demonstrated by the following examples:

EXAMPLE 7

Myocardial Imaging with $^{99m}Tc(acac)_2en(PMe_3)_2^+$

A normal mongrel dog was injected with the complex prepared as in Example 2. Images of the dog were obtained with a high sensitivity collimator. These images clearly show the myocardium, with no washout of the radiopharmaceutical from the myocardium occurring up to 3 hours post injection. Tissue distribution of this complex in normal female Sprague-Dawley rats was computed. These data show that the complex is taken up to a significant degree in the hearts of normal rats (about 2.8% dose/g) and that there is no washout of the radiopharmaceutical for up to 90 minutes. Also, the heart to blood, heart to lung, and heart to liver ratios are very favorable.

This same complex was injected into a normal human volunteer, and excellent images were obtained with a high sensitivity collimator. These images also clearly show the myocardium, with no washout of the radiopharmaceutical from the myocardium occurring up to 6 hours post injection. A second volunteer was injected while at exercise, and the resulting images demonstrate that exercise clearly improves the quality of the myocardial image.

The $^{99m}Tc(III)$ complexes of the present invention provide a radiopharmaceutical uniquely adapted for use in myocardial imaging of humans. These radiopharmaceuticals neither hang up in the blood system nor the liver and yet bind to the heart to provide a positive human heart image.

Accordingly having described our invention,
We claim:

1. A complex comprising a cationic $^{99m}$Tc(III) complex having a reduction potential for the Tc(III)/(II) couple sufficiently negative to prevent in vivo reduction from Tc(III) to Tc(II) in humans having a Tc(III/II) reduction potential electrode at least about as negative as −0.3 volts relative to a Ag/AgCl reference in N,N' dimethyl formamide with 0.5 M tetraethylammonium perchlorate wherein said cationic $^{99m}$Tc(III) complex has the following general formula:

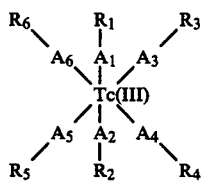

wherein
$A_1$–$A_6$ represent atoms coordinatively bonded to said Tc and at least 3 and no more than 4 of said $A_1$–$A_6$ represent an atom selected from the group consisting of N, O, Cl, S, Br, and the remaining of $A_1$–$A_6$ represent an atom selected from the group consisting of P, As, Te; and
$R_1$–$R_6$ combined with said $A_1$–$A_6$ repesent ligands complexed to said Tc, and wherein when A represents Cl− or Br−, A—R represents only one atom.

2. The complex claimed in claim 1 wherein $A_3$—$R_3$, $A_4$—$R_4$ and $A_5$—$R_5$ collectively represent a tridentate ligand.

3. A method of forming a cationic $^{99m}$Tc(III) complex having a reduction potential for the Tc(III)/(II) couple sufficiently negative to prevent in vivo reduction from Tc(III) to Tc(II) in humans comprising reacting $^{99m}$TcO$_4^-$ with a ligand, said ligand selected from the group consisting of a tetradentate ligand having four ligating atoms at least three of which being selected from the group consisting of N, O, Cl, S, Br, and a tridentate ligand having three ligating atoms selected from the group consisting of N, O, Cl, S, Br to form a Tc(v) compound and subsequently reducing said compound to Tc(III) in the presence of a ligand having ligating atoms selected from the group consisting of P, As, and Te thereby forming said $^{99m}$Tc(III) complex.

4. The complex claimed in claim 1 wherein $A_1$—$R_1$ and $A_2$—$R_2$ both represent a ligand having the following general formula:

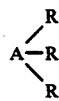

wherein A represents a soft atom and R represents $C_1$–$C_5$ alkyl, a $C_1$–$C_5$ alkyl substituted by a group selected from the groups consisting of hydroxyl, ketone, nitrile, ether, amide and ester groups, phenyl and phenyl substituted with a group selected from the groups consisting of hydroxyl, ether, ester and amide groups and oxy-$C_1$–$C_5$ alkyl.

5. The complex claimed in claim 1 wherein $A_3$—$R_3$, $A_4$—$R_4$, $A_5$—$R_5$ and $A_6$—$R_6$ combined represent a tetradentate ligand having the following general formula:

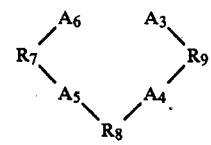

wherein at least two of said $A_3$–$A_6$ represent atoms selected from the group consisting of N, O, Cl, S, Br and $A_1$ and $A_2$ each represent an atom selected from the group consisting of P, As and Te; and wherein $R_7$, $R_8$ and $R_9$ represent $C_1$–$C_{10}$ alkylene, $C_1$–$C_{10}$ alkylene substituted with a group selected from the groups consisting of hydroxyl, ketone, aldehyde, ester, amide, nitrile and carbohydrate groups, arylene, arylene substituted with a group selected form the groups consisting of hydroxyl, ketone, aldehyde, ester, amide, nitrile and carbohydrate groups, $C_1$–$C_4$ alkylenearylene, $C_1$–$C_4$ alkylenearylene substituted with a group selected from the groups consisting of hydroxyl, ketone, aldehyde, ester, amide, nitrile and carbohydrate groups, $C_1$–$C_4$ alkenyl and $C_1$–$C_4$ alkenyl substituted with a group selected from the groups consisting of hydroxyl, ketone, aldehyde, ester, amide, nitrile and carbohydrate groups.

6. The complex claimed in claim 5 wherein $A_3$–$A_6$ all represent hard atoms.

7. The complex claimed in claim 5 wherein $A_3$–$A_6$ represent atoms selected from the group consisting of N, O and S.

8. The complex claimed in claim 7 wherein said tetradentate ligand is a Schiff base ligand.

9. The complex claimed in claim 8 wherein said tetradentate ligand is selected from the group consisting of
(acac)$_2$en, (Sal)$_2$ en
(sal)$_2$phen, (buac)$_2$en, (bzac)$_2$en
(brac)$_2$en,
(acac)$_2$pn.

10. The complex claimed in claim 9 wherein said tetradentate ligand is selected from the group consisting of (acac)$_2$en and (acac)$_2$pn and said $A_1$—$R_1$ and $A_2$—$R_2$ represent ligands selected form the group consisting of tert-butylisonitrile, trimethylphosphine and trimethylphosphite.

11. The complex claimed in claim 6 wherein $A_1$ and $A_2$ represent soft atoms and $A_1$—$R_1$ and $A_2$—$R_2$ represent ligands having the following general formula:

$$\begin{array}{c} R \\ / \\ A-R \\ \backslash \\ R \end{array}$$

wherein R represents $C_1$–$C_5$ alkyl $C_1$–$C_5$ alkyl substituted with a group selected from the groups consisting of hydroxyl, ketone, nitrile, ether, amide and ester groups, phenyl and phenyl substituted with a group selected from the group consisting of hydroxyl, ether, ester and amide groups and oxy-$C_1$–$C_5$ alkyl.

12. The complex claimed in claim 5 wherein $A_1$—$R_1$ and $A_2$—$R_2$ each collectively represent a ligand selected from the group consisting of Cl−, —OH−.

13. The complex claimed in claim 2 wherein said tridentate ligand is selected from the group consisting of:

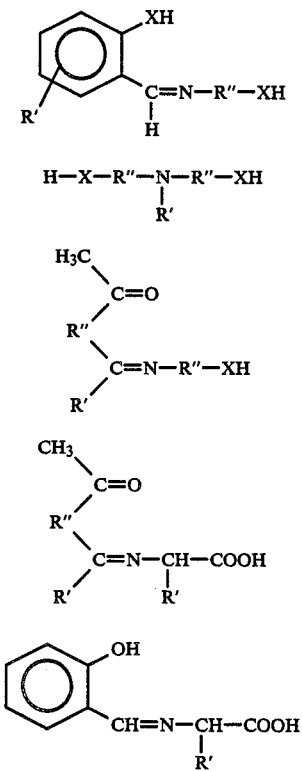

wherein
X represents O or S;
R' represents H or —CH$_3$;
R'' represents C$_1$-C$_3$ alkylene.

14. The method of imaging the heart of a human comprising intravenously applying an effective amount of the complex claimed in claim 1 into said human and detecting radiation emitted from said complex which localizes in the heart of the said human.

15. The method of imaging the heart of a human comprising intravenously applying an effective amount of the complex claimed in claim 4 into said human and detecting radiation emitted from said complex which localizes in the heart of the said human.

16. The method of imaging the heart of a human comprising intravenously applying an effective amount of the complex claimed in claim 5 into said human and detecting radiation emitted from said complex which localizes in the heart of the said human.

17. The method of imaging the heart of a human comprising intravenously applying an effective amount of the complex claimed in claim 6 into said human and detecting radiation emitted from said complex which localizes in the heart of the said human.

18. The method of imaging the heart of a human comprising intravenously applying an effective amount of the complex claimed in claim 7 into said human and detecting radiation emitted from said complex which localizes in the heart of the said human.

19. The method of imaging the heart of a human comprising intravenously applying and effective amount of the complex claimed in claim 8 into said human and detecting radiation emitted from said complex which localizes in the heart of the said human.

20. The method of imaging the heart of a human comprising intravenously applying an effective amount of the complex claimed in claim 9 into said human and detecting radiation emitted from said complex which localizes in the heart of the said human.

21. The method of imaging the heart of a human comprising intravenously applying an effective amount of the complex claimed in claim 10 into said human and detecting radiation emitted from said complex which localizes in the heart of the said human.

22. The method of imaging the heart of a human comprising intravenously applying an effective amount of the complex claimed in claim 11 into said human. and detecting radiation emitted from said complex which localizes in the heart of the said human.

23. The method of imaging the heart of a human comprising intravenously applying an effective amount of the complex claimed in claim 12 into said human and detecting radiation emitted from said complex which localizes in the heart of the said human.

24. The method of imaging the heart of a human comprising intravenously applying an effective amount of the complex claimed in claim 2 into said human and detecting radiation emitted from said complex which localizes in the heart of the said human.

25. The method of imaging the heart of a human comprising intravenously applying an effective amount of the complex claimed in claim 13 into said human and detecting radiation emitted from said complex which localizes in the heart of the said human.

* * * * *